United States Patent [19]

Doss et al.

[11] 4,326,529
[45] Apr. 27, 1982

[54] CORNEAL-SHAPING ELECTRODE

[75] Inventors: James D. Doss; Richard L. Hutson, both of Los Alamos, N. Mex.

[73] Assignee: The United States of America as represented by the United States Department of Energy, Washington, D.C.

[21] Appl. No.: 100,664

[22] Filed: Dec. 5, 1979

Related U.S. Application Data

[63] Continuation-in-part of Ser. No. 909,865, May 26, 1978, abandoned.

[51] Int. Cl.$^3$ ............................................. A61B 17/36
[52] U.S. Cl. ................................................. 128/303.1
[58] Field of Search .................. 128/276, 207.21, 401, 128/402, 305, 399, 783, 240, 303.1, 303.13, 303.14

[56] References Cited

U.S. PATENT DOCUMENTS

| | | | |
|---|---|---|---|
| 603,815 | 5/1898 | Duke | 128/803 |
| 1,108,686 | 8/1914 | Bonis | 128/207.21 |
| 1,364,148 | 1/1921 | Springer | 128/803 |
| 2,126,070 | 8/1938 | Wappler | 128/207.21 |
| 2,347,915 | 5/1944 | Landaver | 128/783 |
| 2,525,381 | 10/1950 | Tower | 128/793 |
| 3,237,623 | 3/1966 | Gordon | 128/24 A |
| 3,307,553 | 3/1967 | Liebner | 128/400 |
| 3,948,269 | 4/1976 | Zimmer | 128/303.1 |
| 3,978,864 | 9/1976 | Smith | 128/404 |
| 3,991,770 | 11/1976 | LeVeen | 128/804 |
| 4,003,383 | 1/1977 | Brück | 128/404 |
| 4,014,333 | 3/1977 | McIntyre | 128/240 |
| 4,140,130 | 2/1979 | Storm | 128/400 |

FOREIGN PATENT DOCUMENTS

222969 6/1910 Fed. Rep. of Germany ...... 128/240

OTHER PUBLICATIONS

An Electrothermal Technique for the Alteration of Corneal Curvature, U.S. Dept. of Energy, Contract W-7405-Eng. 36, LA-7155-MS, Doss et al., Univ. Cal., Los Alamos, New Mexico 87545, 2/78.
Thermal Treatment of Cancer Eye, Dept. of Energy, Univ. California, Doss.
A Technique for the Selective Heating of Corneal Stroma, Doss et al., U.S. Dept. E.R.D.A., Contract W-7405-Eng. 36, U. Cal., Los Alamos, LA-UR78-452.
"Shrinkage Temperature of Eye Collagen", Stringer et al., Native Wellcome Medical Research Inst., Dunedin, New Zealand.
"Thermokeratoplasty Temperature Profile", Shaw et al., Investigative Ophthalmology, pp. 181–185, vol. 13, No. 3, Mar. 1974.
"Alterations in Corneal Morphology Following Thermokeratoplasty", Aquavella, Arch. Ophthalmology-vol. 94, Dec. 1976, pp. 2082–2085.
"Thermokeratoplasty for Keratoconus", Keates et al., Ophthalmic Surgery, Fall, 1975, vol. 6, No. 3, pp. 89–92.
Thermokeratoplasty in the Treatment of Keratoconus, Gasset et al., Amer. J. Ophthalmology, Feb. 1975, pp. 226–232.
'Eye Surgery', Stallard, The Williams and Wilkins Co., Baltimore, Md, 1973, pp. 703–706.

*Primary Examiner*—Robert W. Michell
*Assistant Examiner*—J. Kruter
*Attorney, Agent, or Firm*—Robert W. Weig; Paul D. Gaetjens; Richard G. Besha

[57] ABSTRACT

The disclosure relates to a circulating saline electrode for changing corneal shape in eyes. The electrode comprises a tubular nonconductive electrode housing having an annular expanded base which has a surface substantially matched to a subject corneal surface. A tubular conductive electrode connected to a radiofrequency generating source is disposed within the electrode housing and longitudinally aligned therewith. The electrode has a generally hemispherical head having at least one orifice. Saline solution is circulated through the apparatus and over the cornea to cool the corneal surface while radiofrequency electric current emitted from the electrode flows therefrom through the cornea to a second electrode, on the rear of the head. This current heats the deep corneal stroma and thereby effects corneal reshaping as a biological response to the heat.

15 Claims, 6 Drawing Figures

CORNEAL-SHAPING ELECTRODE

CROSS REFERENCE TO RELATED APPLICATION

This application is a continuation in part of application Ser. No. 909,865, filed May 26, 1978, now abandoned.

BACKGROUND OF THE INVENTION

Field of the Invention

The invention relates to corneal reshaping and more particularly to electrodes utilizing radiofrequency electrical current to heat and thereby induce reshaping of the cornea in animals including humans.

Extreme cases of refractive error, such as those caused by keratoconus, are frequently not correctable by the addition of external refraction. Corneal transplant is the usual remedy. Recent alternatives have been suggested which include modification of the corneal shape by thermal methods which rely upon dramatic shrinkage of corneal collagen in about the 55° to 65° Centigrade (C) range. The use of these thermal methods has been limited by damage to the epithelium and Bowman's membrane, and the temporary nature of the change effected. Each of these problems appear to be related to the thermal dose profile within the cornea which is generated by the conductive heating apparatus. Temperatures reached in the epithelium are relatively high while temperatures reached in the deeper stromal collagen are below the critical shrinkage temperature needed. A wide variability in treatment results exists which is probably caused by unintentional variation in individual techniques in administering thermal treatments, particularly in the length of time that heat is applied.

The use of heat to alter the shape of the cornea is generally referred to as thermokeratoplasty (TKP). A device called a thermokeratophore has been used by several medical researchers. The essential part of the device is a cylindrical metal probe that is electrically preheated to some desired temperature; usually in the range of between about 90° and 130° C. The probe is then applied directly to the cornea for one to two seconds. The cornea is heated by thermal conduction from the metal probe; surface temperature at the cornea is significantly higher than deeper (stromal) temperature. Measurements of the temperature profile achieved in rabbit corneas are described by E. L. Shaw and A. R. Gasset in "Thermokeratoplasty (TKP) Temperature Profile," J. Invest. Ophthalmol. 13, No. 3, 181–186 (1974). For example, a two second application of a 90° C. probe produced epithelial and endothelial temperatures of about 69° and 53° C. respectively. Central corneal stroma would have been treated to about 60–62° C., probably high enough for shrinkage to occur. The rabbit cornea is relatively thin, being only about 400 microns thick. Shrinkage down to depths of about 200 microns might be sufficient for a thin cornea such as that of the rabbit, buut would probably only cause minimal or transient change in shape when corneal thickness exceeds 400 microns. Human corneal thickness typically varies from 580 microns centrally to 1000 microns at the periphery. The reason the invention uses radiofrequency electric current for heating is that it is essential to penetrate at least a few hundred microns in depth to effect corneal changes in larger mammals, such as man.

OBJECTS OF THE INVENTION

One object of the present invention is to provide correction of complex corneal refractive errors virtually impossible to correct with external refraction.

Another object of the present invention is to provide corrections to corneas without conventional surgery.

Yet another object of the present invention is to provide correction of ordinary corneal refractive errors and thus eliminate the need for external correction.

One advantage of the invention is that superficial corneal tissue is cooled and thereby protected while allowing deeper corneal tissue to be heated sufficiently.

Another advantage of the instant invention is that the temperature increases effected within the cornea are sufficiently deep that they enter the collagen fibers which, result in more permanent changes in corneal shape than prior devices achieved.

SUMMARY OF THE INVENTION

In accordance with the present invention there is provided an apparatus for changing corneal shape comprising an electrically conductive element positionable near to without touching the corneal surface of an eye. Conductive fluid is circulated between the conductive element and the corneal surface and a current return electrode is connected to the subject's body. An alternating voltage is produced between the conductive element and the current return electrode to provide an alternating current flow through the conductive fluid. This generates heat within the corneal tissue, heat being removed from superficial corneal tissue by the circulating conductive fluid; deeper corneal tissue reaches a higher temperature level than superficial tissue. In a preferred embodiment there is provided a tubular monconductive electrode housing having a longitudinal axis and at one end an annular expanded base. The base has a surface substantially matched to the subject corneal surface of the human eye or the eye of the size of animal to which the instrument is to be applied. A tubular conductive electrode having a longitudinal axis is positioned within the electrode housing. The electrode has a generally hemispherical head disposed in the vicinity of the annular end of the housing, but is positioned therein so as not physically touch the cornea of the person or animal to be treated. The electrode head has at least one orifice to provide circulation of a saline fluid therethrough. A pump reservoir and conduit is utilized to circulate saline fluid through the electrode and back through the housing. A radiofrequency generator is electrically connected to the electrode structure and to the rear of the head of the person or animal to be treated. The electrode structure is positioned on the surface of the eye and radiofrequency energy therefrom is applied to the eye for a selected period of time in order to effect the desired changes in the corneal shape of the eye.

BRIEF DESCRIPTION OF THE DRAWINGS

Other objects and advantages of the instant invention will be apparent to those skilled in the art from the following description with reference to the appended drawings wherein like numbers denote like parts and wherein.

DETAILED DESCRIPTION OF THE PREFERRED EMBODIMENT OF THE INVENTION

Figure 1:
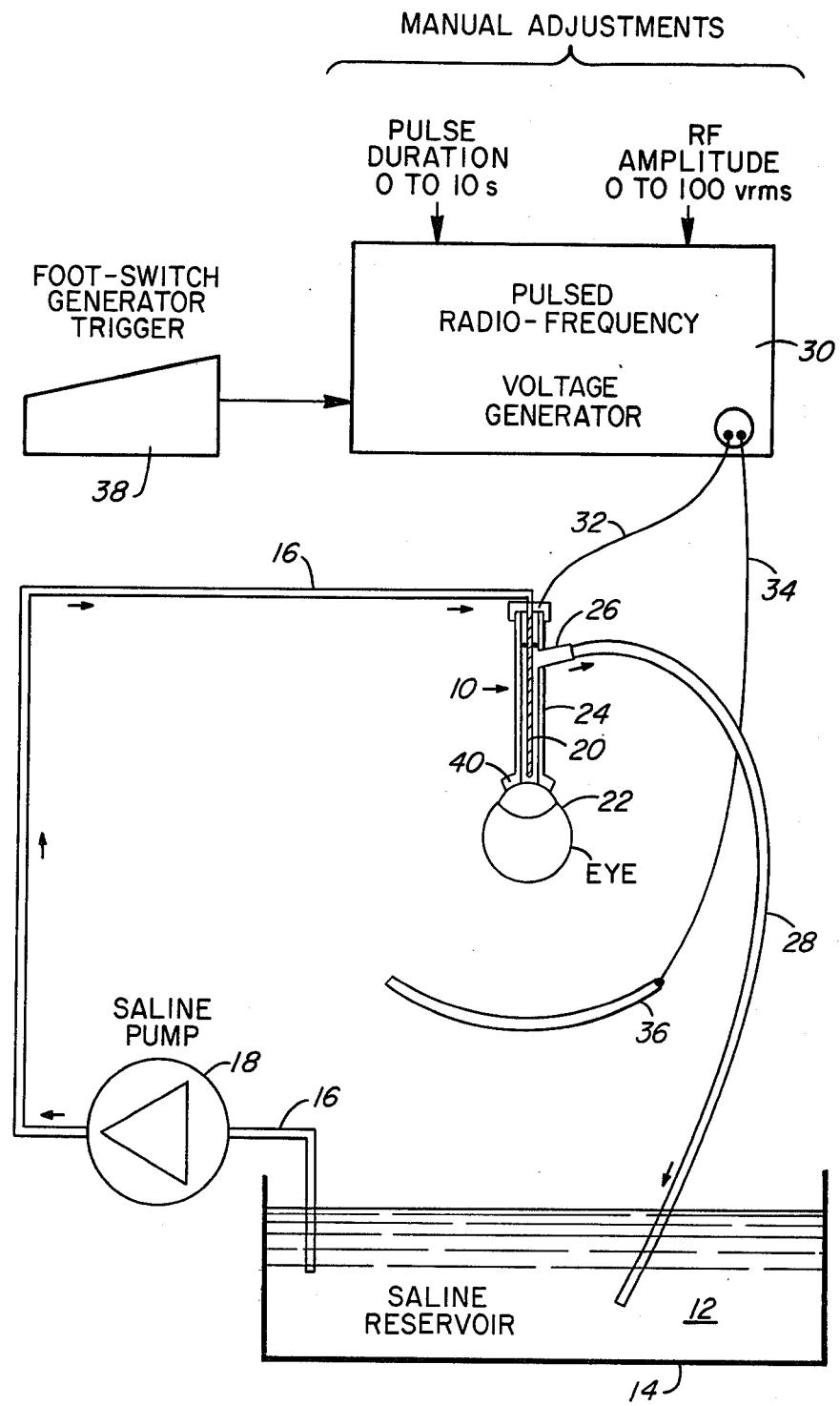
FIG. 1 shows a system in accordance with the present invention for effecting corneal change in animals including humans.
Figure 2:
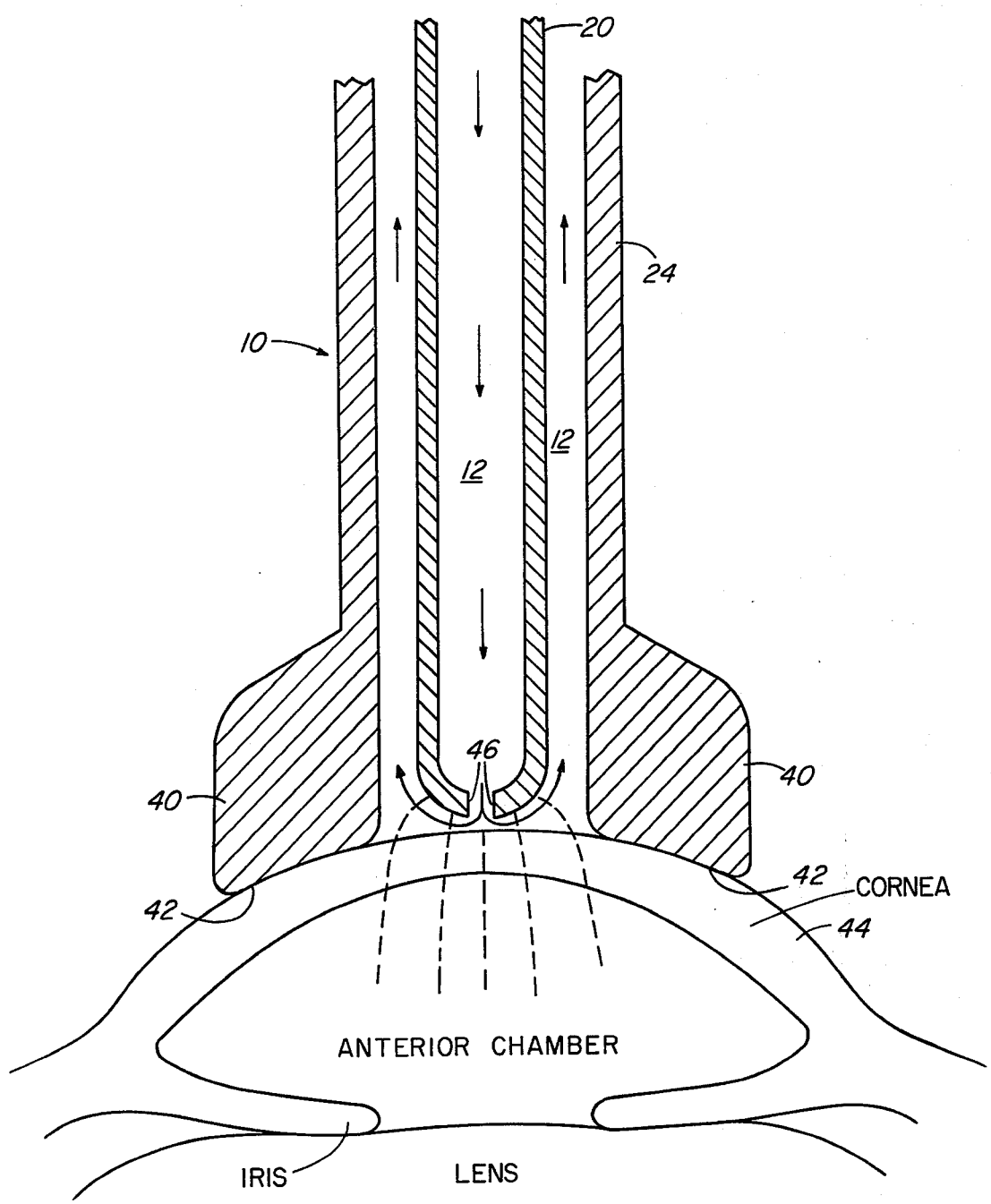
FIGS. 2, 3, and 4 show embodiments of electrodes in accordance with the present invention.

FIGS. 1 and 2 schematically show a system in accordance with the invention utilizing an electrode structure 10 through which a saline solution 12 is circulated from a reservoir 14 through tubing 16 by a pump 18. The saline solution preferably comprises isotonic saline but may be hypotonic or hypertonic to alter the electrical resistivity of the saline when desired. Importantly, the saline solution provides electrical conduction to the corneal surface for the radiofrequency current and acts as a coolant for layers of the cornea nearer the surface which provides protection of superficial tissue simultaneous with deeper heating of corneal tissues which are the tissues needed to be heated in order to effect relatively permanent changes in corneal shape.

Saline solution 12 passes through a tubular electrode 20 in the electrode structure 24 and reaches the surface of an eye 22. It then is forced between the electrode 20 and a nonconductive tubular electrode housing 24 and out through a nipple 26 communicating with the interior of the tubular nonconductive electrode housing 24. Nipple 26 is attached to a second tubing 28 which returns the saline solution 12 back to saline reservoir 14. Fluid flow may alternatively run between electrode 20 and housing 24 onto the eye and return to a reservoir through electrode 20. Too, a housing could be conductive and inner tubing nonconductive.

The tubular electrode 20 is electrically connected to a radiofrequency generator 30 by a conductive element 32. A second conductive element 34 is electrically connected between the radiofrequency generator 30 and an electrode 36 affixed to the rear of the head of the person or animal to provide a current return path. A foot switch 38 is utilized to initiate operation of the generator 30. Typically the radiofrequency generator will produce a 2 MHz electric current but any radiofrequency current between about 100 KHz and about 10 MHz producing between about 20 and 60 Vrms for a duration of from about one to about 10 seconds will work. It will be appreciated by those skilled in the art that different current levels and electrode dimensions will be utilized for different corneal depths and that current density decreases as a function of corneal depth. Decrease in current densities is essentially a function of electrode configuration. In general, a larger electrode results in more uniform heating.

Figure 5:
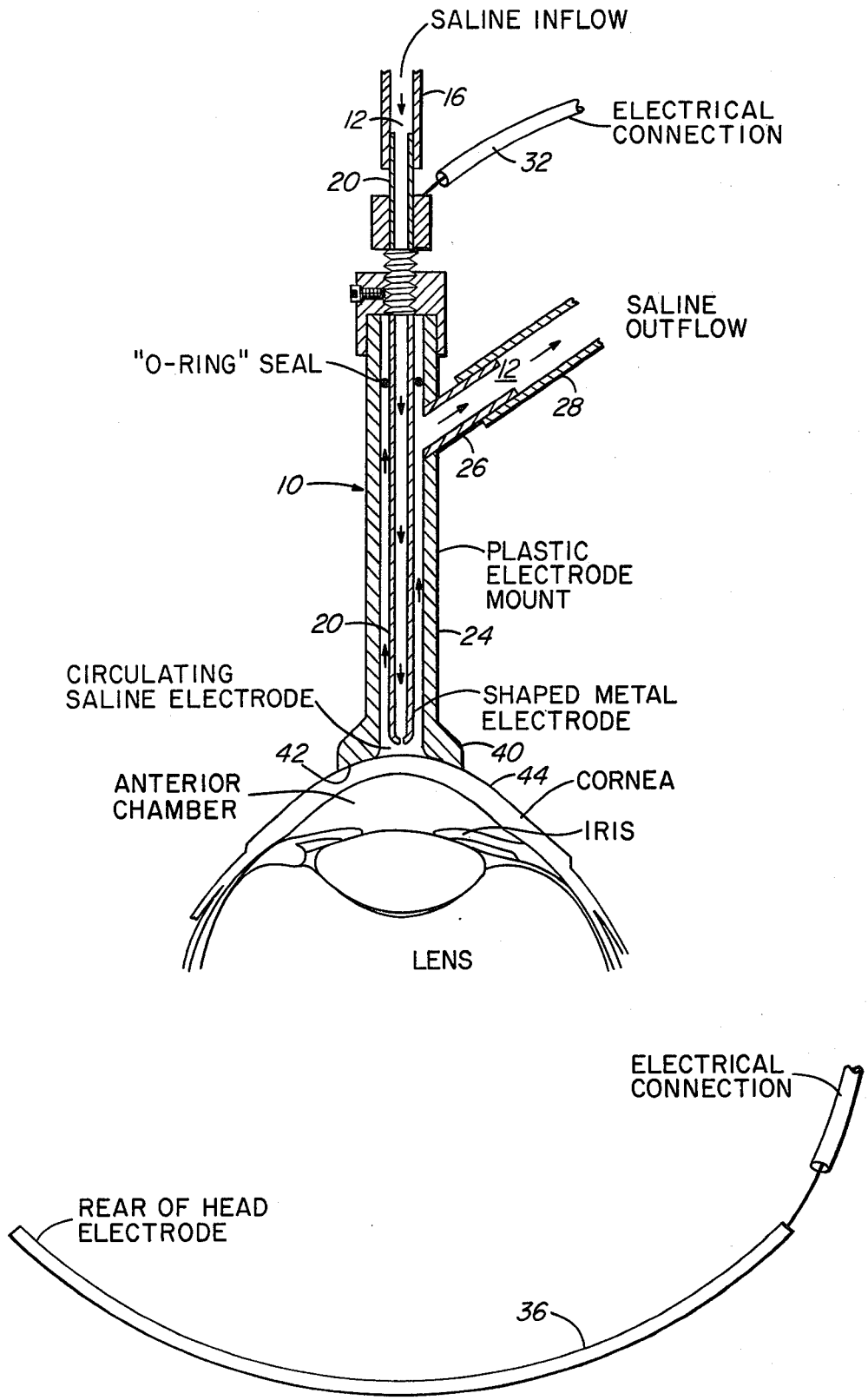
FIG. 5 illustrates total electrode structure.

A problem unsolved by prior art thermokeratophores is that the thermal energy deposited in the epithelium is greater than that in the deeper stroma and some epithelium heat must be removed if that portion of the cornea is not to be overheated. This problem is solved by using electrically conductive coolant 12; as cooling is accomplished by the flow of isotonic saline solution over the surface of the eye. As seen in FIG. 5, structure 10 comprises a tubular nonconductive electrode housing 24 having an enlarged annular base portion 40 which has a surface 42 fittable to the surface of the cornea 44 of the person or animal to be treated. Saline solution 12 is circulated down through tubular electrode 20 through an orifice defined by wall 46, best seen in FIG. 2, against the surface of the cornea 44 and back through the conduit established between the inner diameter of electrode housing 24 and the outer diameter of electrode 20. The radiofrequency electric current field flowing from electrode 20, indicated by the dashed lines, enters the cornea 44 to selectively heat and thereby thermally reform internal regions of the cornea.

Figure 3:
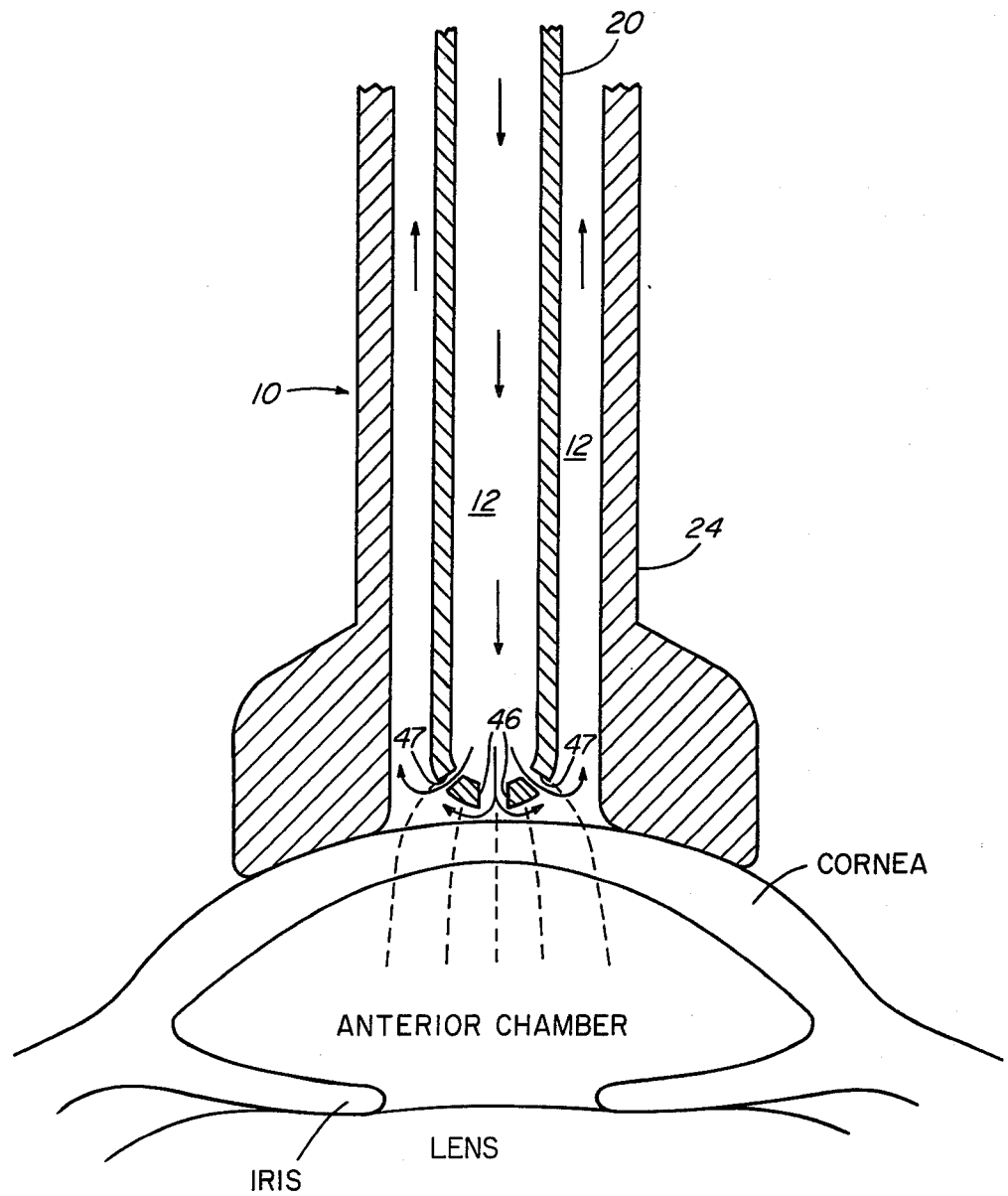

FIG. 3 shows a very similar electrode structure to that of FIG. 2 except that a plurality of orifices having additional walls 47 are shown. The addition of a plurality of such orifices which are preferably in a circumferential pattern about the original central orifice having walls 46 is to provide coolant flow into the region at the edge of the circular area of the cornea which is heated.

Figure 4:
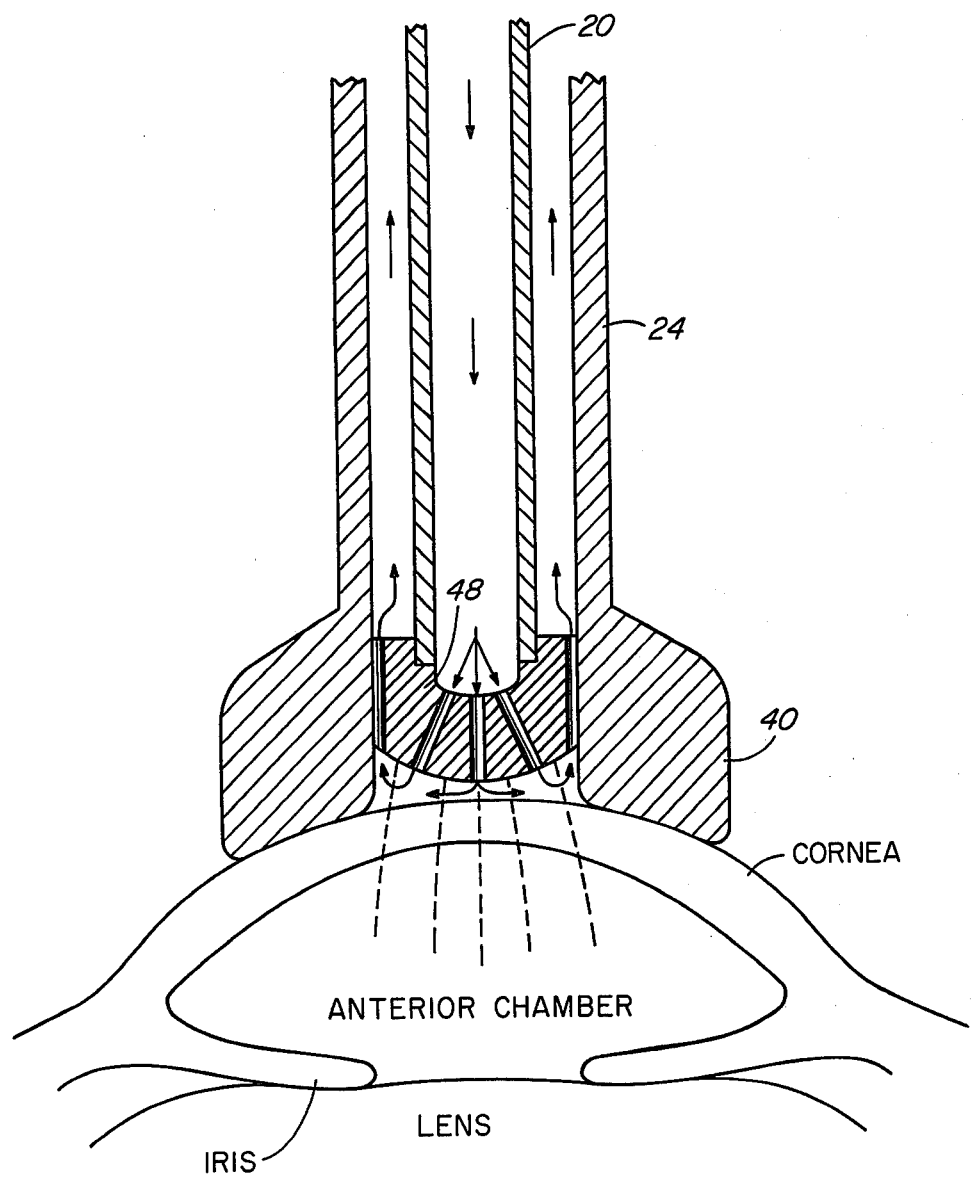

As seen in FIG. 4, a separate but electrically conductive head 48 may be attached to tubular electrode 20. This head has a slightly different orifice structure than that shown in FIG. 3 and the recirculation of the saline solution back up between the electrode and the electrode housing is affected by the spacing of the head away from the annular base region 40 of the housing 24. Head 48 produces different cooling and electric field characteristics than FIG. 2 or FIG. 3 electrodes. Those skilled in the art will recognize that the head of the electrode need not be hemispherical, but may be any configuration capable of directing radio frequency energy into a cornea in sufficient strength and with appropriate distribution to accomplish the desiderata of the invention.

The invention was tested and in one test freshly excised pig eyes were placed in isotonic saline, with 5% dextran at approximately 4° C. These eyes had vertical diameters of from about 21 to about 24 mm and a corneal thickness in the range of about 800 to about 1,000 microns. The temperatures in the eye were monitored by copper-Constantan thermocouples comprising 25 and 50 micron diameter wire. Thermocouples used in the circulating saline electrode (CSE) portion of the experiment were coated with 5 microns of parylene-C insulation to minimize electrical interference with the temperature measurement. Temperature was monitored by a Brush model 816 multi-point recorder, accurate to approximately 1° C. over the range of interest. In each case, heat was delivered either by a conduction probe, i.e., a "simulated" thermokeratophore, a brass rod with a 3 mm tip, preheated to 90° C., or the CSE system of FIG. 1. Time duration of heating was preset between from 0 to 10 seconds on the CSE system, and was measured for both heating methods on the Brush 816 graph. The eye with thermocouples placed at appropriate levels in the cornea, anterior chamber, and lens was placed in a plastic jig. The preheated metal conduction probe or the CSE probe was then placed on the cornea over the implanted thermocouples. Most of the eyes were heated 30 to 40 times, some with both conduction and CSE probes. Some variability in temperature readings, largely due to variations in placement of thermocouples were seen in different eyes.

Figure 6:
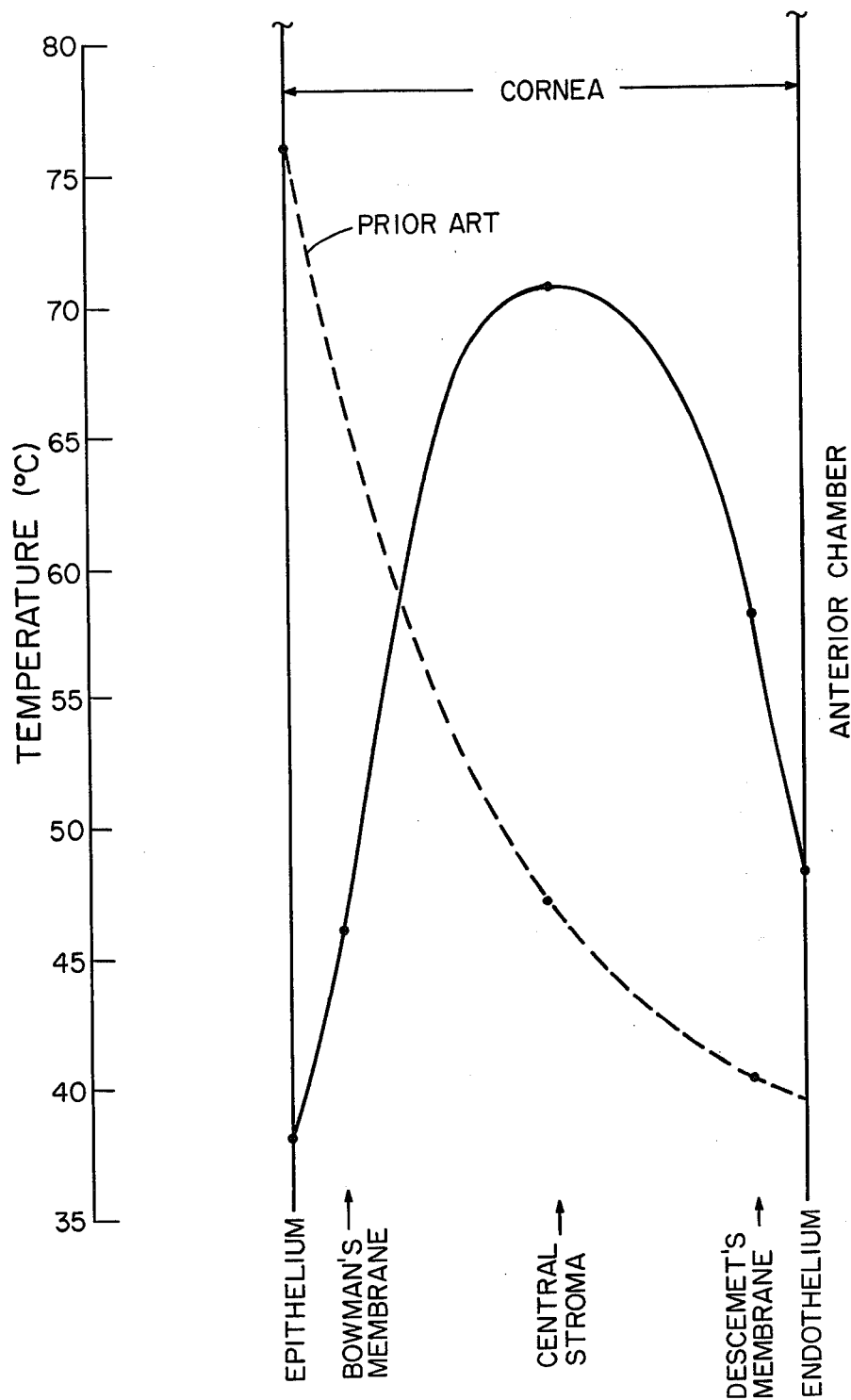
FIG. 6 shows the undesirable temperature profile generated with conventional conduction heating and a temperature profile reached within the cornea during the process of utilizing an electrode in accordance with the present invention.

With reference to the temperature profiles presented in FIG. 6, typically uncertainties are epithelium ±1° C., posterior of Bowman's membrane ±3° C., central stroma ±5° C., anterior of Descemet's membrane ±5° C. and endothelium ±3° C. As is apparent from FIG. 6, conventional conduction-TKP, represented by the dashed line, not only causes rather high temperatures in the epithelium and Bowman's membrane, but it fails to cause the central stroma to reach critical shrinkage temperature for corneas which exceed a thickness of about 300 microns. This typically leads to shrinkage in only a superficial portion of the stromal collegen, which may partially explain the transitory nature of alterations in corneal shape that have been reported by those utilizing this method.

The temperature profile for CSE seen in FIG. 6, represented by the solid line, shows that the invention results in far lower thermal dose to the epithelium and Bowman's membrane. In addition, temperature levels in the central stroma are indeed sufficient for shrinkage to occur. This means that more permanent changes in corneal shape than those realized from the conduction probe are achieved using the CSE device. For the CSE profile shown in FIG. 6, temperature increase was approximately 4° C. in the anterior chamber and 0.8° C. in the lens. Since use of the apparatus of the invention is amenable to electronic control of both applied voltage and duration of pulse to approximately ±1%, repeatability is also much improved over the conduction-TKP method.

It is important to note that electrode dimensions, saline temperature and saline flow rate must also be duplicated in each application for substantially the same results. It will be apparent to those skilled in the art that thin corneas will be treated better by smaller electrodes because their electric current density profiles decay rapidly enough to avoid overheating the endothelium.

Using an electrode structure of the invention, a small (2–3 mm effective diameter) CSE electrode is placed on the cornea and a much larger electrode is placed on the opposite side of the head. An electric current (f=2 MHz) is generated which flows through the cornea, between the two electrodes. Current density (J) decreases with an increase in distance from the small electrode. As is known, power density (P) is the product of current density (J) squared and the electrical resistivity of the tissue (p):

$$P(\text{watts/cm}^3) = J^2(\text{amperes}^2/\text{cm}^4)\rho(\text{ohm·cm})$$

Because of its low water content, electrical resistivity of corneal tissue is higher than the resistivity of the aqueous humor in the anterior chamber. This results in a sharp decrease in heat generated at the endothelium-aqueous interface. Too, there is a much more gradual decrease in power generation through the cornea, due to a general reduction in current density as distance is increased from the electrode. These factors tend to keep the endothelium at a lower temperature than the stroma, as does thermally-induced convection in the anterior chamber.

Cross sectional views of CSE probes on corneas are shown in FIGS. 2, 3, and 4. The saline serves not only to cool the corneal surfaces, it is also an integral part of the electrical circuit. The combination saline-metal electrode structure provides electric fields which may be shaped by adjustment of the geometry and resistivity of each medium. The particular embodiments shown can be adjusted to provide an electric field which is highest in the center, along the axis of the metal electrode 20. This combination electrode is preferable to a homogeneous metallic cylinder, which has relatively high fields at the edges where cooling is difficult to accomplish.

In an experiment using a live dog, an ophthalmologist's retinoscope readings before heating were −3.50,+4.00 at 90°. These readings are interpreted as follows:

1. The first figure (−3.50) is the power of a spherical lens, (in diopters) that would be required to correct for all but the astigmatic error that exists for this eye.
2. The second pair of figures indicates that the astigmatism in this eye can be corrected by the addition of a cylindrical lens of +4 diopters power, whose major axis is aligned with the 90 degrees meridian of the eye. (Facing the eye, 90 degrees is at 12 o'clock; 0 degrees is at 3 o'clock.)

The readings on astigmatism indicated that the eye had four diopters less refracting power in the horizontal meridian than in the vertical meridian. It appeared that an application of heat to shrink the cornea either at 0 or 180° might increase the "steepness" in these regions and therefore reduce astigmatism. Actual results depend largely on the elasticity and interactions of stromal collagen fibers. As was expected with the placement of the CSE probe at 180° (9 o'clock) with an applied voltage of 30 Vrms, and treatment durations increasing from 1.5 to 5.0 seconds, a moderate ring-shaped opacity was seen in the treatment region. Retinoscopy after the five heat applications yielded readings of −2.50,+1.00 at 110°. Thus, the astigmatism had shifted axis slightly and decreased in magnitude to 25% of its original value. In addition, the net refractive error had been reduced by one diopter.

The animal was examined by a veterinarian and an ophthalmologist three days after CSE treatment. At this time, the opacity of the treated region of the cornea had become less prominent but blood vessels had infiltrated the sclera. No vessels were apparent in the cornea, which had a generally good appearance to a casual visual examination. An ophthalmologist's slit-lamp examination did reveal some abnormality of the endothelial cells, which are located on the inner surface of the cornea. This is important, since endothelial cells do not regenerate and there is a minimum concentration of these cells which are required to preserve the cornea.

During the same examination, retinoscopy revealed that the net refractive error of the cornea was further reduced but that the astigmatic correction had relaxed somewhat. The new readings were −1.50,+2.00 and 110°. Retinoscopy data taken 10 weeks later yielded readings of Plano, −1.00, 90° which can be interpreted as follows: all of the animal's net power error and 75% of the astigmatic error have been corrected; there was no apparent tendency for the eye to revert to its prior condition. In addition, no opacity could be seen in the cornea after 10 weeks.

The various features and advantages of the invention are thought to be clear from the foregoing description. However, various other features and advantages not specifically enumerated will undoubtedly occur to those versed in the art, as likewise will many variations and modifications of the preferred embodiment illustrated, all of which may be achieved without departing from the spirit and scope of the invention as defined by the following claims.

What we claim is:

1. A circulating saline electrode for changing corneal shape comprising:
   a tubular nonconductive electrode housing having a longitudinal axis and at one end an annular expanded base, said base having a surface substantially matched to the subject corneal suface of an eye;

a tubular conductive electrode having a longitudinal axis positioned within and longitudinally aligned with said tubular housing, said electrode having agenerally hemispherical head disposed in the vicinity of said annular base of said housing, adapted to be positioned near to but not physically touching a cornea against which said housing may be placed, said electrode head having at least one orifice therein:

means for circulating an electrically conductive coolant through said tubular electrode and said orifice therein and thence through said tubular housing; and means for applying electromagnetic energy at a radiofrequency wavelength through said tubular electrode to selectively heat the subject cornea and thereby change its shape.

2. The invention of claim 1 wherrein said electrode head orifice is essentially axially aligned with said tubular electrode and centered substantially in said generally hemispherical head.

3. The invention of claim 2 wherein said electrode head has additional orifices dispensed essentially in a circumferential pattern about said first mentioned orifice to aid corneal cooling in any corneal region near the periphery of the generally hemispherical electrode head.

4. The invention of claim 1 wherein said electrode head has a larger outside diameter than the outside diameter of said tubular electrode and a smaller outside diameter than the inside diameter of said annular electrode housing base.

5. The invention of claim 1 wherein said tubular electrode comprises stainless steel.

6. The invention of claim 1 wherein said coolant comprises an isotonic saline solution.

7. The invention of claim 1 wherein said coolant comprises a non-isotonic saline solution.

8. An apparatus for changing corneal shape comprising:

an electrically conductive element positionable near to without touching the corneal surface means for circulating electrically conductive fluid between said electrically conductive element and said corneal surface;

means comprising a current return electrode connectable to a portion of the subject's body; and means for producing an alternating electric voltage between said electrically conductive element and said current return electrode to provide an alternating electric current flow through said circulating electrically conductive fluid and the corneal tissue of said eye thereby generating heat within said corneal tissue, surface heat being removed from superficial corneal tissue by convective heat transfer effected by said circulating electrically conductive fluid, thereby causing deeper corneal tissues to reach a higher temperature level than more superficial corneal tissues nearer the corneal surface.

9. The invention of claim 8 wherein said electrically conductive element and said fluid circulating means comprise inner and outer tubular elements.

10. The invention of claim 9 wherein fluid flow is onto the corneal surface through said inner tubular element and from the corneal surface between said inner and outer tubular elements.

11. The invention of claim 9 wherein fluid flow is onto the corneal surface from between said inner and outer tubular elements and from the corneal surface through said inner tubular element.

12. The invention of claim 9 wherein said tubular elements are essentially cylindrical.

13. The invention of claim 9 wherein said inner element is conductive and said outer element is nonconductive.

14. The invention of claim 9 wherein said inner element is nonconductive and said outer element is conductive.

15. The invention of claim 8 wherein said electrically conductive element comprises a hollow tubular conductive electrode fixedly disposed about the axis of rotation of a cylindrically tubular, nonconductive electrode housing, so that said electrically conductive fluid flows through said hollow tubular conductive element, exiting through an orifice disposed at the end of said electrically conductive element positionable near to the corneal surface, said fluid returning to a reservoir through the annular space between said tubular conductive electrode and said tubular nonconductive electrode housing, said tubular nonconductive housing having an annular base contactable with and fittable on the corneal surface to substantially limit leakage of said electrically conductive fluid away from the region of the cornea through which heat is to be applied.

* * * * *